(12) United States Patent
Shin et al.

(10) Patent No.: US 7,682,314 B2
(45) Date of Patent: Mar. 23, 2010

(54) BLOOD PRESSURE METER USING VISCOELASTICITY OF CUFF AND MOBILE TERMINAL HAVING THE SAME

(75) Inventors: Sang-hoon Shin, Seongnam-si (KR); Hyouk-ryeol Choi, Gunpo-si (KR); Ja-choon Koo, Seoul (KR); Kyung-ho Kim, Yongin-si (KR); Ki-wang Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 877 days.

(21) Appl. No.: 11/410,015

(22) Filed: Apr. 25, 2006

(65) Prior Publication Data
US 2006/0253041 A1 Nov. 9, 2006

(30) Foreign Application Priority Data
May 3, 2005 (KR) .................. 10-2005-0037048

(51) Int. Cl.
*A61B 5/02* (2006.01)
(52) U.S. Cl. .................... 600/499; 600/485; 600/490
(58) Field of Classification Search ............ 600/499; 606/202
See application file for complete search history.

(56) References Cited
U.S. PATENT DOCUMENTS

| | | | |
|---|---|---|---|
| 4,873,987 A * | 10/1989 | Djordjevich et al. | ......... 600/485 |
| 5,031,630 A * | 7/1991 | Hirano et al. | ............... 600/493 |
| 5,119,823 A | 6/1992 | Teramoto et al. | |
| 5,511,551 A | 4/1996 | Sano et al. | |
| 5,807,266 A | 9/1998 | Itonaga et al. | |
| 2004/0010198 A1* | 1/2004 | Yamakoshi et al. | ......... 600/499 |

* cited by examiner

Primary Examiner—Patricia C Mallari
(74) Attorney, Agent, or Firm—Sughrue Mion, PLLC

(57) ABSTRACT

A blood pressure meter using a viscoelastic cuff, and a mobile terminal having the blood pressure meter. The blood pressure meter includes a blood pressure sensor for measuring variation in blood pressure, a blood flow sensor for measuring variation in blood flow, a cuff that elastically compresses a body part and decompresses the body part due to its viscoelasticity, and a control unit that analyzes signals measured by the blood pressure sensor and the blood flow sensor and calculates blood pressure. The blood pressure meter is detachably connected to a mobile terminal body, and can be small and portable. It is possible to measure the blood pressure precisely even when the cuff is fitted onto a finger, thereby improving the reliability of the blood pressure measurement. By using the viscoelasticity of the cuff and auxiliary decompressing, it is possible to check the blood pressure at all times.

5 Claims, 12 Drawing Sheets

BLOOD PRESSURE METER USING VISCOELASTICITY OF CUFF AND MOBILE TERMINAL HAVING THE SAME

CROSS-REFERENCE TO RELATED PATENT APPLICATION

This application claims the benefit of Korean Patent Application No. 10-2005-0037048, filed on May 3, 2005, in the Korean Intellectual Property Office, the disclosure of which is incorporated herein in its entirety by reference.

BACKGROUND OF THE INVENTION

1. Field of the Invention

The present invention relates to a blood pressure meter and a mobile terminal having the blood pressure meter and, more particularly, to a blood pressure meter made more portable by simplifying the structure of a cuff for compressing or decompressing a body part of a testee, and a mobile terminal having the blood pressure meter.

2. Description of the Related Art

Blood pressure is classified into arterial pressure, capillary pressure, and venous pressure, but the term is usually used to refer to arterial pressure. Arterial pressure varies during each heartbeat. The blood pressure when a ventricle of the heart contracts and pushes blood out to an artery is referred to as systolic pressure. The systolic pressure is the maximum blood pressure in the blood vessels. When the ventricle of the heart expands and does not push blood out, the artery walls are elastic and maintain some blood pressure. This pressure is referred to as diastolic pressure. The diastolic pressure is the minimum blood pressure. The difference between the systolic pressure and the diastolic pressure is referred to as the pulse pressure.

Blood pressure varies depending on the conditions. Accordingly, it is difficult to clearly determine blood pressure with one measurement. The blood pressure measured on an empty stomach right after waking is referred to as basic pressure. The basic pressure is helpful for medical diagnosis. In real life, it is necessary to measure the blood pressure several times under various conditions. Therefore, there is a need for a portable electronic blood pressure meter which can be handled at home by general users.

An apparatus which can keep a constant contact area between a finger and a cuff regardless of the thickness of the finger is disclosed in U.S. Pat. No. 5,511,551, entitled "Cuff for blood pressure meter." A foldable cuff is disclosed in U.S. Pat. No. 5,807,266, entitled "Finger-type Blood Pressure Meter with a Flexible Foldable Finger Cuff." An apparatus which can bring a cuff into close contact with a finger by manually pulling the cuff is disclosed in U.S. Pat. No. 5,119,823, entitled "Cuff Wrapping Apparatus for Blood Pressure Meter."

The above-mentioned patent inventions have a common feature that a cuff is fitted onto a finger and compressed or decompressed with air pressure. However, since a volume of air must be injected into the cuff in order to finely adjust the pressure of the cuff, the size of the cuff is increased. Miniature air-pressure cuffs are possible but are not capable of precise decompression for measuring blood pressure. In addition, mechanical parts such as a pump, a drive source, and a valve, for adjusting the pressure of the cuff, hinder the decrease in size of the blood pressure meter. On the other hand, in order to check blood pressure for health care at all times, the portability of the blood pressure meter should be improved.

Therefore, there is a need for a small, lightweight blood pressure meter having a simple cuff which can replace the air-pressure cuff.

SUMMARY OF THE INVENTION

The present invention provides a blood pressure meter having a cuff with a simple structure which can replace a conventional air-pressure cuff, to decrease the size and improve the portability of the blood pressure meter, and a mobile terminal having the blood pressure meter.

According to an aspect of the present invention, there is provided a blood pressure meter comprising: a pressure adjusting member including a cuff that is elastically deformed at the time of fitting the cuff onto a body part of a testee to compress the body part and impede blood flow, and whose compressing pressure to the body part is decreased due to its viscoelasticity over time; a blood pressure sensor that measures the pressure of the body part at the time of compression and decompression of the pressure adjusting member; and a control unit that analyzes a signal measured by the blood pressure sensor at the time of compression and decompression of the pressure adjusting member and calculates the blood pressure of the testee.

The blood pressure meter according to the present invention may further comprise a blood flow sensor for measuring variation in blood flow. Here, the control unit may analyze signals measured by the blood pressure sensor and the blood flow sensor at the time of compression and decompression of the pressure adjusting member and may calculate the blood pressure of the testee.

According to another aspect of the present invention, there is provided a mobile terminal having a blood pressure meter, the mobile terminal comprising: a mobile terminal body having a display unit for displaying the measured blood pressure; and a blood pressure measuring unit that measures blood pressure and is connected to the mobile terminal body. Here, the blood pressure measuring unit includes: a pressure adjusting member having a cuff that is elastically deformed at the time of fitting the cuff onto a body part of a testee to compress the body part and impede blood flow, and whose compressing pressure to the body part is decreased due to its viscoelasticity over time; a blood pressure sensor that measures the pressure of the body part at the time of compression and decompression of the pressure adjusting member; a blood flow sensor for measuring variation in blood flow; and a control unit that analyzes signals measured by the blood pressure sensor and the blood flow sensor at the time of compression and decompression of the pressure adjusting member and calculates the blood pressure of the testee.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF ILLUSTRATIVE, NON-LIMITING EMBODIMENTS OF THE INVENTION

Figure 1:
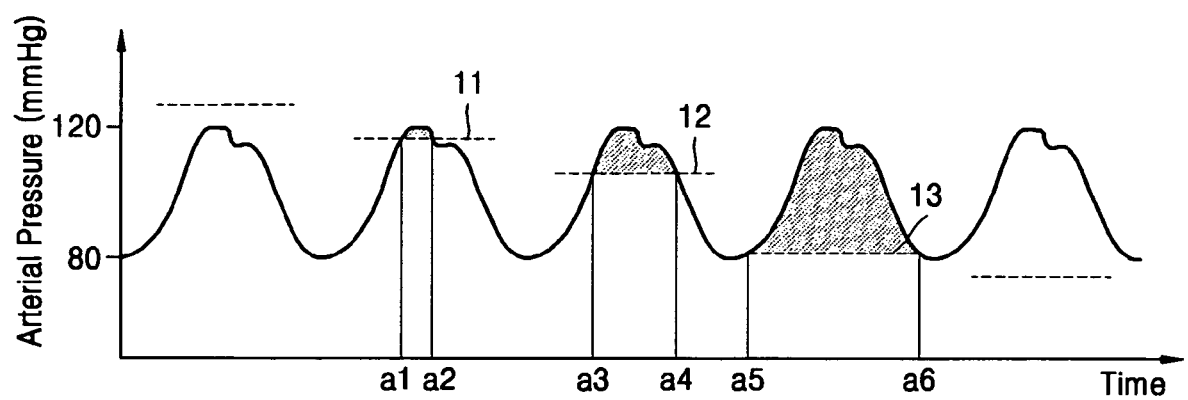
FIG. 1 is a graph illustrating a Korotkoff measuring method in a blood pressure meter according to an exemplary embodiment of the present invention.

Hereinafter, exemplary embodiments of the present invention will be described in detail with reference to the accompanying drawings. The exemplary embodiments of the present invention are not limited to the attached drawings, but may be modified in form without departing from the scope of the present invention.

The pressure in the blood vessel when blood in a ventricle of a heart is sent out to a main artery by contraction of the heart muscle is referred to as the systolic pressure or the maximum blood pressure, and is usually about 120 mmHg. The pressure in the blood vessel when the heart expands is referred to as the diastolic pressure or the minimum blood pressure, and is usually about 80 mmHg. Blood pressure measuring methods can be roughly classified into direct measuring methods and indirect measuring methods. In a direct measuring method, a catheter is inserted into the artery and connected to a manometer or the like. Then, the pressure in the artery is directly measured. Indirect measuring methods are further classified into Korotkoff measuring methods, oscillometric measuring methods, and Doppler ultrasonography measuring methods.

In an exemplary embodiment of the present invention, a cuff made of a viscoelastic material is used in place of an air-pressure cuff. A pressure adjusting means according to an exemplary embodiment of the present invention includes the cuff made of a viscoelastic material.

According to an exemplary embodiment of the present invention, the pressure adjusting means includes a cuff that is elastically deformed at the time of fitting the cuff onto a body part of a testee, to compress the body part to impede blood flow, and whose compression decreases over time. The pressure adjusting means compresses and decompresses the body part, and the blood pressure is measured with a blood pressure sensor.

The blood pressure sensor may be coupled to or separated from the cuff. The blood pressure sensor measures the pressure of the cuff body part at the time of compression and decompression of the pressure adjusting means. The blood pressure sensor may be a contact type or a non-contact type. A blood pressure sensor that can measure dynamic oscillation, such as an acceleration sensor, may be suitably used for the oscillometric measuring method shown in FIG. 2. The blood pressure sensor may directly output the operational pressure by the blood pressure or may output the operational pressure as a voltage. The blood pressure sensor can be embodied in various forms, which are well known to those skilled in the art, and detailed descriptions of which will be omitted.

According to an exemplary embodiment of the present invention, the blood pressure sensor is provided on a contact surface between the cuff and the body part, and measures variations in contact pressure between the cuff and the body part. The control unit controls the blood pressure sensor and analyzes signals measured by the blood pressure sensor to calculate the blood pressure of the testee at the time of compression and decompression of the pressure adjusting means.

FIG. 1 is a graph illustrating the Korotkoff measuring method in the blood pressure meter according to an exemplary embodiment of the present invention. The dotted line in FIG. 1 denotes the compressing pressure of the cuff $200a$ or $200b$, the X axis denotes time, and the Y axis and the solid curve denote the blood pressure, which indicate the practical pressure in the blood vessel.

Supposing that the systolic pressure is 120 mmHg and the diastolic pressure is 80 mmHg, the blood pressure shown in the Y axis oscillates between 120 mmHg and 80 mmHg with a period corresponding to the heartrate. When the compressing pressure of the cuff $200a$ or $200b$ shown by the dotted line is 120 mmHg or more, the blood flow is blocked and no stethoscopic sound is heard. When the compressing pressure of the cuff $200a$ or $200b$ is decreased and reaches the vicinity of 120 mmHg, a turbulent flow of blood is started from the time point a1 to the time point a2, and a stethoscopic sound is heard. When the compressing pressure of the cuff $200a$ or $200b$ is decreased to the position indicated by a reference numeral 12 and becomes smaller than 120 mmHg, the stethoscopic sound becomes distinctly greater from the time point a3 to the time point a4. When the compressing pressure of the cuff $200a$ or $200b$ is decreased to the vicinity of 80 mmHg at the position indicated by a reference numeral 13, the stethoscopic sound becomes less from the time point a5 to the time point a6. When the compressing pressure of the cuff $200a$ or $200b$ is further decreased below 80 mmHg, the blood vessels are completely open and the turbulent flow, as well as the stethoscopic sound, disappears. The compressing pressure of the cuff $200a$ or $200b$ from the time point a1 to the time point a2 where the stethoscopic sound starts is the maximum blood pressure, which is indicated by the reference numeral 11. A healthy testee has a maximum blood pressure of about 120 mmHg. The compressing pressure of the cuff $200a$ or $200b$ from the time point a5 to the time point a6 where the stethoscopic sound disappears is the minimum blood pressure, which is indicated by the reference numeral 13. A healthy testee has a minimum blood pressure of about 80 mmHg.

In the Korotkoff measuring method, the stethoscopic sound starting at the time point when the maximum blood pressure is measured, and the stethoscopic sound disappearing at the time point when the minimum blood pressure is measured, are sensed with a stethoscope. A tester reads out the blood pressure measured by the blood pressure sensor 600 while hearing the stethoscopic sound with the stethoscope, and measures the maximum blood pressure and the minimum blood pressure.

In an exemplary embodiment of the present invention, a blood flow sensor 900 senses the blood flow corresponding to the stethoscopic sound. The control unit 950 controlling the blood flow sensor 900 and the blood pressure sensor 600 automates the blood pressure measuring process. An example of the blood flow sensor 900 includes a sound pressure sensor.

In an exemplary embodiment of the present invention, the blood flow sensor includes a sound pressure sensor which measures Korotkoff sounds. The control unit, which controls the blood flow sensor and the blood pressure sensor and analyzes the signals measured by the blood flow sensor and the blood pressure sensor to calculate the blood pressure, calculates the blood pressure using the Korotkoff measuring method.

Although not shown in the drawings, the Doppler ultrasonography measuring method will now also be described. The phenomenon that a sound frequency increases when the sound source moves toward an observer, and the sound frequency decreases when the sound source moves away from the observer, is called the Doppler effect. The phenomenon occurs in all waves. The phenomenon can be applied to the medical field for measuring blood flow speed. An ultrasonic wave is emitted into blood vessels from an emission unit of an ultrasonic sensor. When the Doppler effect of the ultrasonic wave reflected by red corpuscles is measured with a reception unit of the ultrasonic sensor, the blood flow speed can be obtained. After the blood vessel is blocked by the compression of the cuff, the cuff is decompressed to allow the blood to start flowing, and signals due to the Doppler Effect are captured. At that time point, the blood pressure measured by the blood pressure sensor is the maximum blood pressure.

In an embodiment of the present invention, the blood flow sensor includes an ultrasonic sensor for measuring the Doppler effect of the ultrasonic wave reflected by the red corpuscles. The control unit, which controls the blood flow sensor and the blood pressure sensor, and analyzes the signals measured by the blood flow sensor and the blood pressure sensor to calculate the blood pressure, calculates the blood pressure using the Doppler ultrasonography measuring method.

Figure 2:
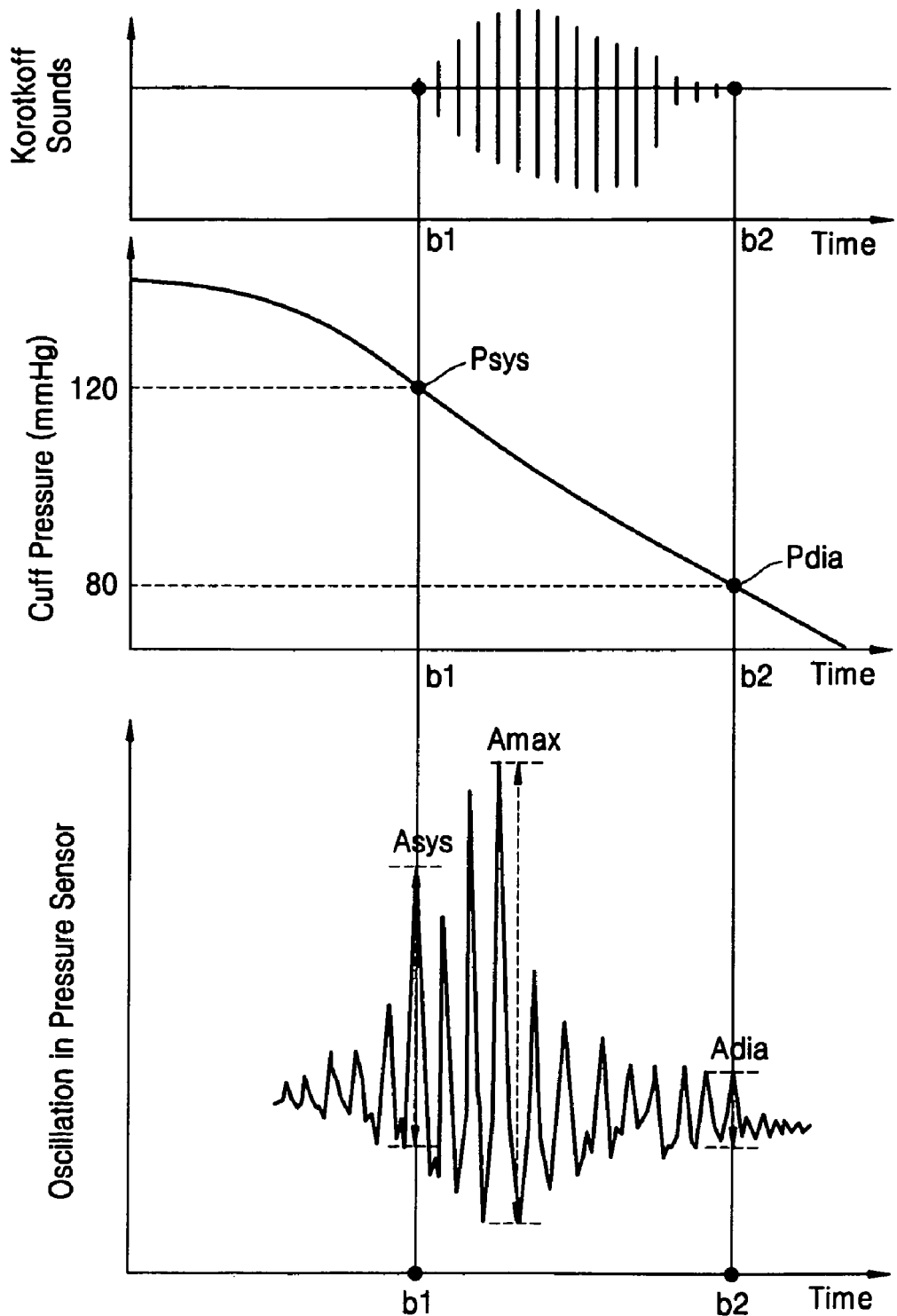
FIG. 2 is a graph illustrating an oscillometric measuring method in a blood pressure meter according to an exemplary embodiment of the present invention.

FIG. 2 is a graph illustrating the oscillometric measuring method in the blood pressure meter according to an exemplary embodiment of the present invention. The uppermost graph indicates the Korotkoff sound over time. The intermediate graph indicates the pressure of the cuff 200a or 200b, which is in equilibrium with the blood pressure. The lowermost graph indicates the amplitude of vibration of the blood pressure sensor 600.

In the oscillometric method, the magnitude of pressure oscillations generated by the cuff 200a or 200b when it is compressed and then slowly decompressed is sensed by the blood pressure sensor 600, to measure the blood pressure. The conversion relationship between the amplitude of vibration as the amplitude of the pressure oscillation and the blood pressure is calibrated in advance.

The oscillometric method is further classified into two kinds of methods. In the first kind of oscillometric method, the blood pressure at the time point b1 when the amplitude of vibration increases rapidly is considered to be the maximum blood pressure, and the blood pressure at the time point b2 when the amplitude of vibration decreases rapidly is considered to be the minimum blood pressure. The systolic pressure is calculated from the amplitude of vibration Asys measured at the time point b1 and the conversion relationship between the amplitude of vibration Asys and the blood pressure. The diastolic pressure is calculated from the amplitude of vibration Adia measured at the time point b2 and the conversion relationship between the amplitude of vibration Adia and the blood pressure.

In the second kind of oscillometric method, the blood pressure at the time point when the amplitude of vibration corresponding to 50% of the maximum amplitude of vibration Amax is generated is considered to be the systolic pressure, and the blood pressure at the time point when the amplitude of vibration corresponding to 75% of the maximum amplitude of vibration Amax is generated is considered to be the diastolic pressure. Here, 50% and 70% are referred to as characteristic ratios. The characteristic ratios differ by 10% to 20% between persons.

The oscillometric measuring method can measure even low blood pressures at which the Korotkoff sound is not captured, because heartbeats always cause vibration. In the oscillometric measuring method, since the amplitude of vibration is measured with the blood pressure sensor 600, and the maximum blood pressure and the minimum blood pressure are measured using the characteristic ratios obtained through clinical experiments, it is possible to measure the blood pressure even when no blood flow sensor is provided.

In an exemplary embodiment of the present invention, the control unit calculates the blood pressure of the testee by using the oscillometric measuring method.

In an exemplary embodiment of the present invention, the cuff 200a or 200b may be fitted to the wrist, upper arm, finger, or other body part. When the cuff is fitted in a ring shape to the finger of a testee, it is very portable.

When the blood pressure is measured using a finger blood pressure meter, signals are measured at the artery of the finger which is thinner than the artery of the upper arm. As a result, the signal to noise ratio (S/N) is small. Noise due to movement of the finger has a great influence on the vibration signals of the blood pressure sensor 600. Since the finger is an extremity of the human body, the variation in blood pressure and the variation in blood flow have a close correlation. Therefore, when the cuff 200a or 200b is fitted to a finger, the blood flow sensor 900 may be used to calculate the blood pressure along with the blood pressure sensor 600. That is, it is possible to improve the signal to noise ratio (S/N) of the signal measured by the blood pressure sensor 600 by providing the blood flow sensor 900 along with the blood pressure sensor 600.

In an exemplary embodiment of the present invention, the pressure adjusting means may further include an auxiliary decompressing means for further enhancing the amount of decompression of the cuff 200a or 200b due to the viscoelasticity. The auxiliary decompressing means functions mechanically or electrically. By utilizing the viscoelasticity of the cuff 200a and the auxiliary decompressing means, the compressing and decompressing conditions corresponding to the health condition of the testee can be prepared. The cuff 200a or 200b according to an exemplary embodiment of the present invention is smaller than the conventional air-pressure cuff, but can perform stable decompression.

The blood flow sensor 900 is coupled to the cuff 200a or 200b or fitted to the outside thereof. When the blood flow sensor 900 is coupled to the cuff 200a or 200b, the structure of the blood pressure meter can be simplified. As a result, the blood flow sensor 900 measuring variation in impedance at the body part fitted with the cuff 200a or 200b due to variation in blood flow can be embodied.

In an exemplary embodiment of the present invention, the blood flow sensor includes first, second, third, and fourth terminals sequentially coming contact with the body part in the blood flow direction. By applying a reference voltage across the first and fourth terminals and measuring the voltage across the second and third terminals, it is possible to measure the variation in impedance at the cuff body part due to the variation in blood flow.

In an exemplary embodiment of the present invention, the control unit checks with the blood pressure sensor whether the blood flow is impeded at the time of compression of the pressure adjusting means, captures with the blood pressure at the time point when the blood flow starts again during the decompression of the pressure adjusting means, and uses the signal measured by the blood pressure sensor at the time point when the blood flow starts again to calculate the systolic pressure.

Figure 9A:
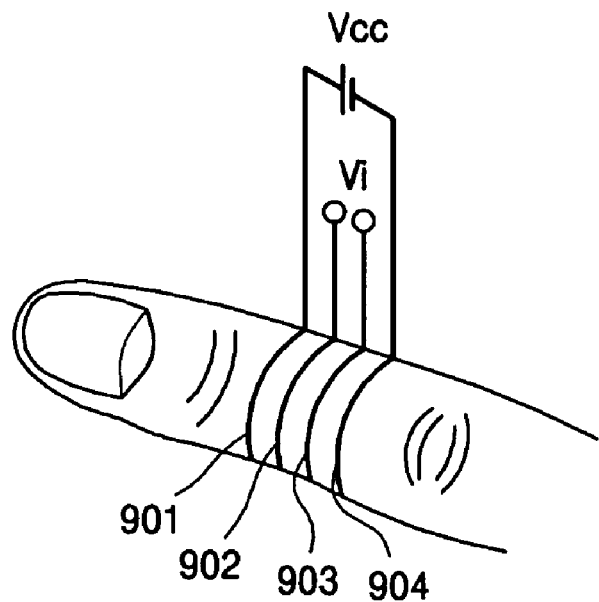
FIG. 9A is a perspective view illustrating an impedance measurement principle of a blood flow sensor according to an exemplary embodiment of the present invention.

Referring to FIG. 9A, when the body part fitted with the cuff 200a or 200b is a finger, the first, second, third, and fourth terminals 901, 902, 903, and 904 are provided separately in a ring shape around the finger. The reference voltage Vcc is applied across the first terminal 901 and the fourth terminal 904. The variation in blood flow varies the impedance of the finger. The variation in impedance is measured as the voltage Vi across the second terminal 902 and the third terminal 903.

Figure 9B:
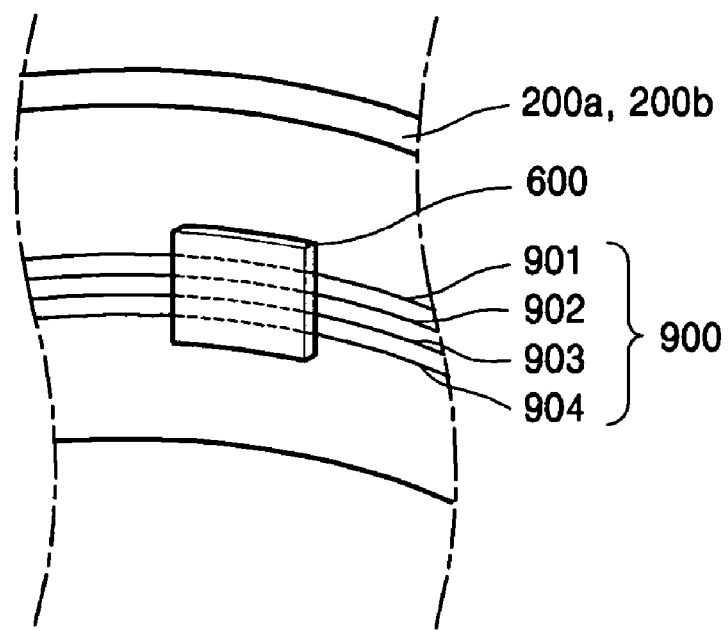
FIG. 9B is a partial perspective view of the cuff fitted with the blood flow sensor.

Referring to FIG. 9B, the cuff 200a or 200b fitted with the blood flow sensor 900 is shown partially exploded. The blood flow sensor 900 is attached to the cuff 200a or 200b. The blood flow sensor 900 includes the first, second, third, and fourth terminals 901, 902, 903, and 904. The blood pressure sensor 600 is provided on the blood flow sensor 900.

Figure 9C:
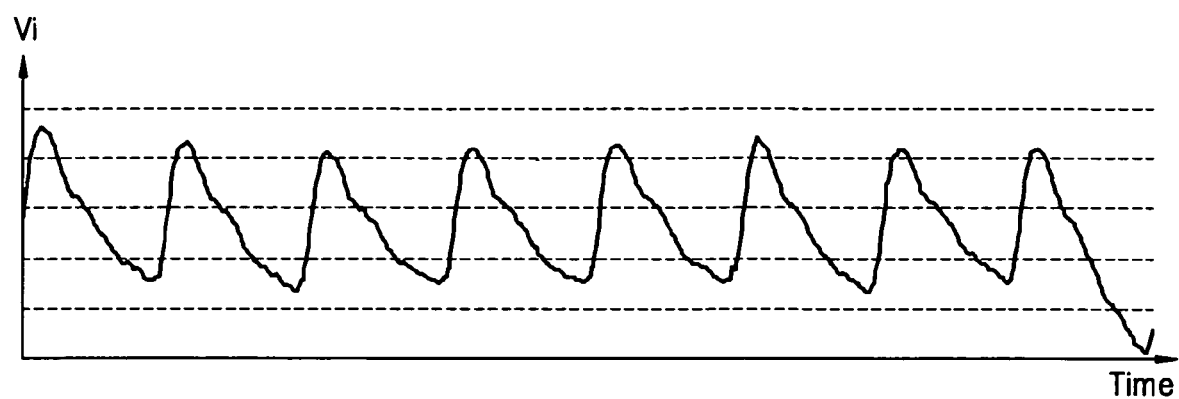
FIG. 9C is a graph illustrating the voltage across second and third terminals.

FIG. 9C shows the voltage Vi across the second terminal 902 and the third terminal 903 due to pulsation of the blood flow. The blood flow sensor 900 is not limited to the type shown, and may be embodied in various ways to measure impedance.

Now, the viscoelasticity of the cuff 200a or 200b according to the exemplary embodiment of the present invention will be described.

An elastic solid quickly returns to its initial state in accordance with Hooke's Law, when the external force resulting in the deformation is removed. However, a polymer compound or a poly-crystalline body returns more slowly to its initial state. This is because of a viscoelastic behavior, involving both elasticity and viscosity. The viscoelastic behavior is expressed in a dynamic model in which a spring and a damper are combined. Dynamic models are classified into a Voigt model in which the spring and the damper are combined in parallel, and a Maxwell model in which the spring and the damper are combined in series.

An example of the viscoelastic cuff is "VHB tape" made by 3M Co.

Figure 3A:
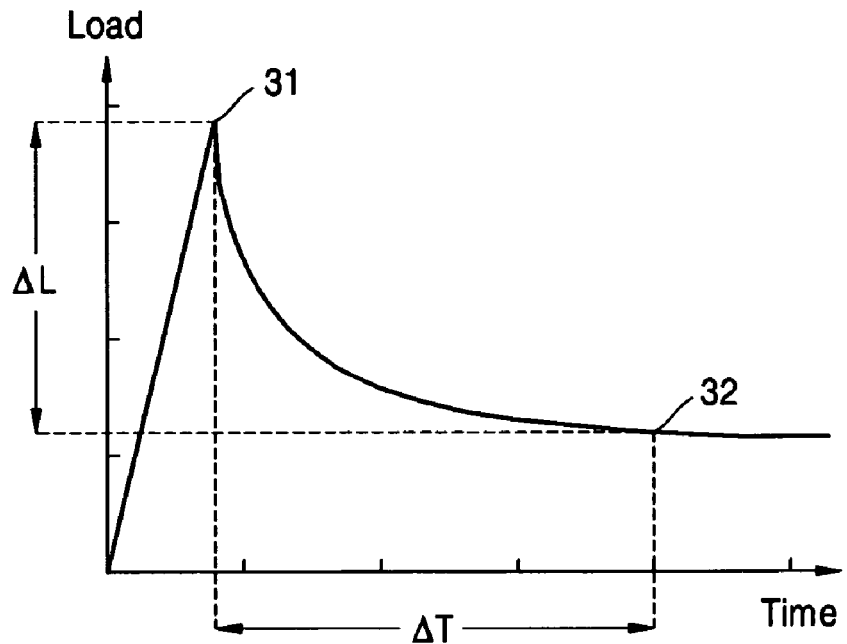
FIGS. 3A and 3B are graphs illustrating viscoelasticity of a cuff according to an exemplary embodiment of the present invention.

FIG. 3A is a graph obtained by applying load to a viscoelastic material to expand it, and measuring the variation in load over time while maintaining a constant deformation. FIG. 3A shows the elasticity of the cuff 200a or 200b, in which the load is increased in proportion to the elastic deformation from the initial time to the time point indicated by a reference numeral 31. The load is decreased by ΔL over time even when the elastic deformation of the cuff 200a or 200b is maintained after the time point 31. The compressing pressure acts up to the time point 31 with the elasticity of the cuff 200a or 200b. Thereafter, the load is decreased by ΔL after a time ΔT with the viscosity of the cuff 200a or 200b. The compressing pressure indicated by a reference numeral 32 remains in the body part fitted with the cuff 200a or 200b.

Figure 3B:
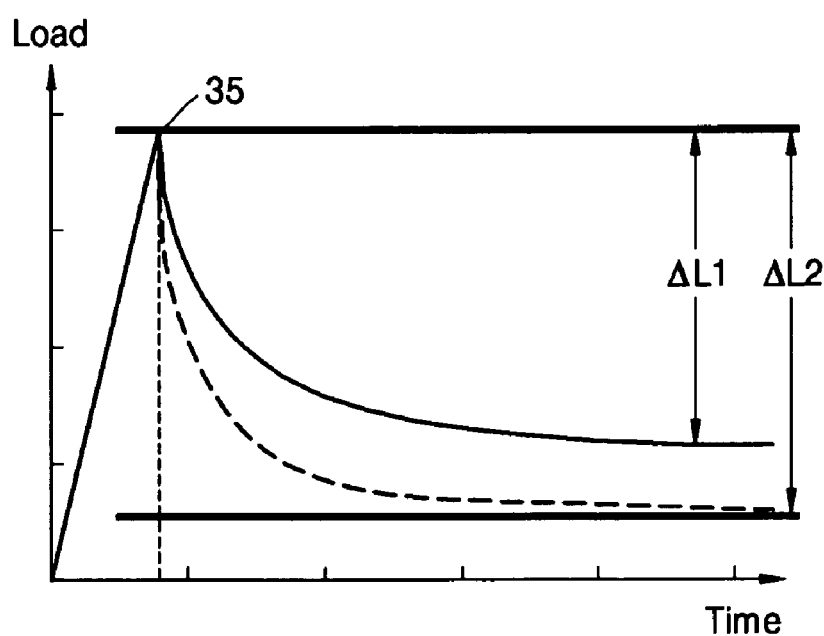

FIG. 3B is a graph illustrating the viscoelastic behavior of the cuff 200a or 200b when the auxiliary decompressing means according to an exemplary embodiment of the present invention is provided. The body part is compressed with the compressing pressure indicated by a reference numeral 35 with the elasticity of the cuff 200a or 200b. Thereafter, the body part is decompressed by ΔL1 only due to the viscosity of the cuff 200a or 200b. When the auxiliary decompressing means is provided along with the cuff 200a or 200b, the amount of decompression is increased to ΔL2.

Figure 4A:
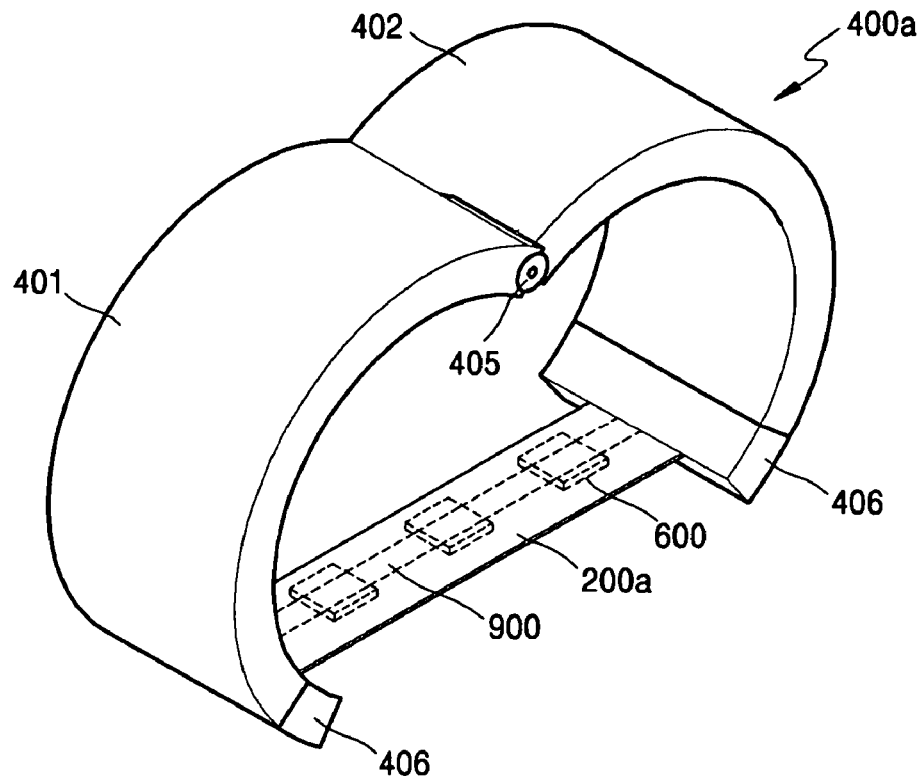
FIG. 4A is a perspective view illustrating a cuff of the blood pressure meter according to an exemplary embodiment of the present invention before fitting the cuff.
Figure 4B:
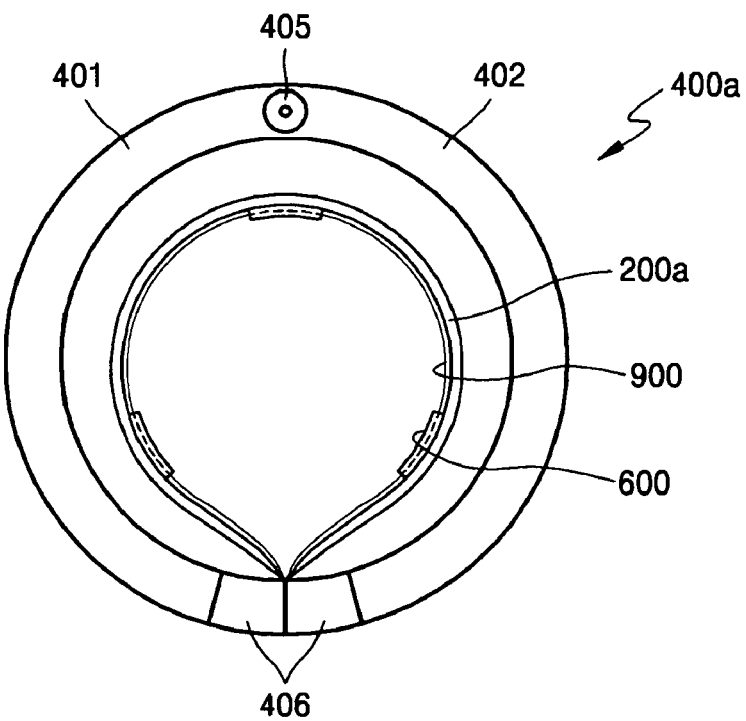
FIG. 4B is a plan view illustrating the cuff after fitting the cuff.

FIG. 4A is a perspective view illustrating the cuff 200a in the blood pressure meter according to an exemplary embodiment of the present invention before fitting the cuff 200a. FIG. 4B is a plan view illustrating the cuff 200a after fitting the cuff 200a.

In an exemplary embodiment of the present invention, the pressure adjusting means includes a cuff fitting member having first and second pieces of which both ends of the cuff are fixed and lockers are provided at one ends, of which the other ends are coupled to each other with a hinge member.

At the time of fitting the cuff, the first and second pieces are locked to each other through the lockers. At the time of removing the cuff, the first and second pieces are unlocked and opened about the hinge member.

The cuff fitting member 400a includes a pair of semicircular rings having the first and second pieces 401 and 402. The first and second pieces 401 and 402 are rotatably coupled to each other through the hinge member 405. The cuff 200a is made of a viscoelastic material in a band shape. The ends of the cuff 200a are fixed respectively to the ends of the first and second pieces 401 and 402. When the cuff 200a is fitted to the testee, the first and second pieces 401 and 402 are rotated about the hinge member 405. The rotation of the first and second pieces 401 and 402 applies tension to expand the cuff 200a. The expanded cuff 200a comes in contact with the body part of the testee and the first and second pieces 401 and 402 are rotated in the locking direction. The ends of the first and second pieces 401 and 402 are provided with the locker 406, which locks the rotation of the cuff fitting member 400a. The expanded cuff 200a can easily surround the body part, and generates the compressing pressure with its elastic restoring force, thereby impeding the blood flow. When the cuff 200a is fitted on a finger, the finger is positioned inside the cuff 200a shown in FIG. 4B. The blood pressure sensor 600 is interposed between the cuff 200a and the finger to measure the blood pressure. The blood flow sensor 900 is interposed between the cuff 200a and the finger to sense the blood flow. The body part is decompressed over time due to the viscoelasticity of the cuff 200a, and thus the blood begins to flow again. When the blood flow sensor 900 senses the blood flow resuming, the control unit 950 receives the signal measured by the blood pressure sensor 600 and calculates the maximum blood pressure. The blood pressure may be measured using any one of the above-mentioned methods.

The pressure adjusting means may further include an auxiliary decompressing means. As an example of the auxiliary decompressing means, a cuff interference member is provided in the cuff fitting member.

In an exemplary embodiment of the present invention, the pressure adjusting means further includes a cuff interference member that is rotatably provided in the cuff fitting member. The cuff interference member contacts and interferes with the cuff in the direction in which the cuff comes in close contact with the body part at the initial time of fitting the cuff, and then is rotated in the opposite direction over time. The cuff interference member further enhances the amount of decompression of the cuff due to the viscoelasticity.

In an exemplary embodiment of the present invention, the pressure adjusting means further includes a cuff interference member that is slidably provided in the cuff fitting member. The cuff interference member contacts and interferes with the cuff in the direction in which the cuff comes in close contact with the body part at the initial time of fitting the time, and then slides in the opposite direction over time. The cuff interference member further enhances the amount of decompression of the cuff due to the viscoelasticity.

Figure 5A:
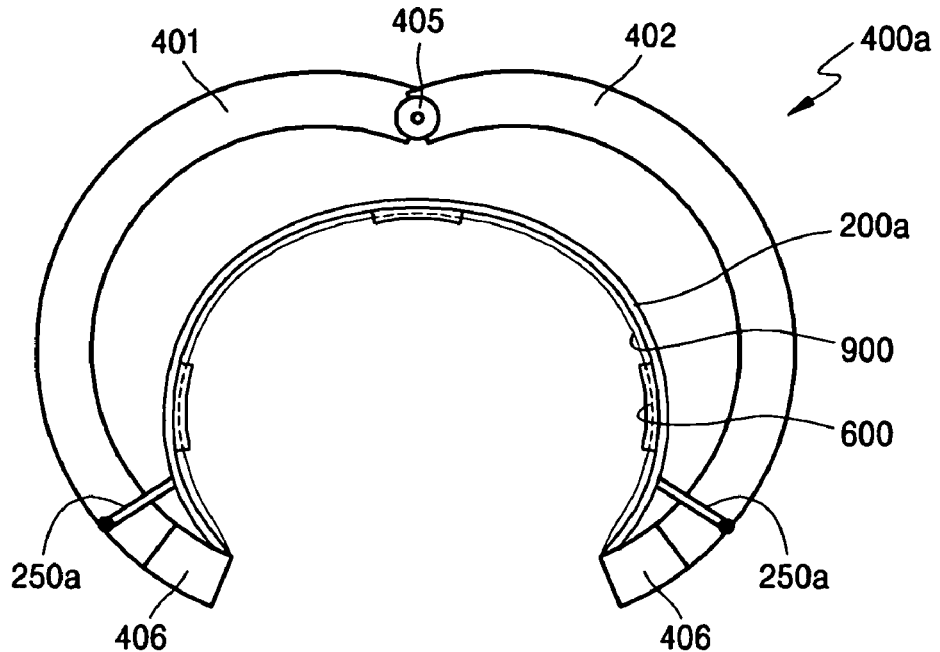
FIG. 5A is a plan view illustrating a cuff interference member according to an exemplary embodiment of the present invention before fitting the cuff.
Figure 5B:
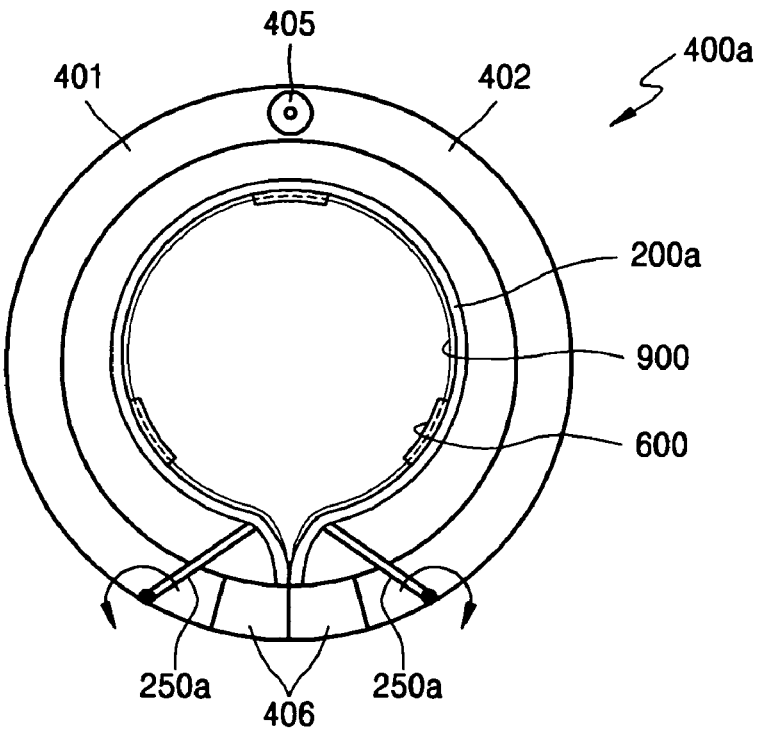
FIG. 5B is a plan view illustrating the cuff interference member after fitting the cuff.
Figure 6A:
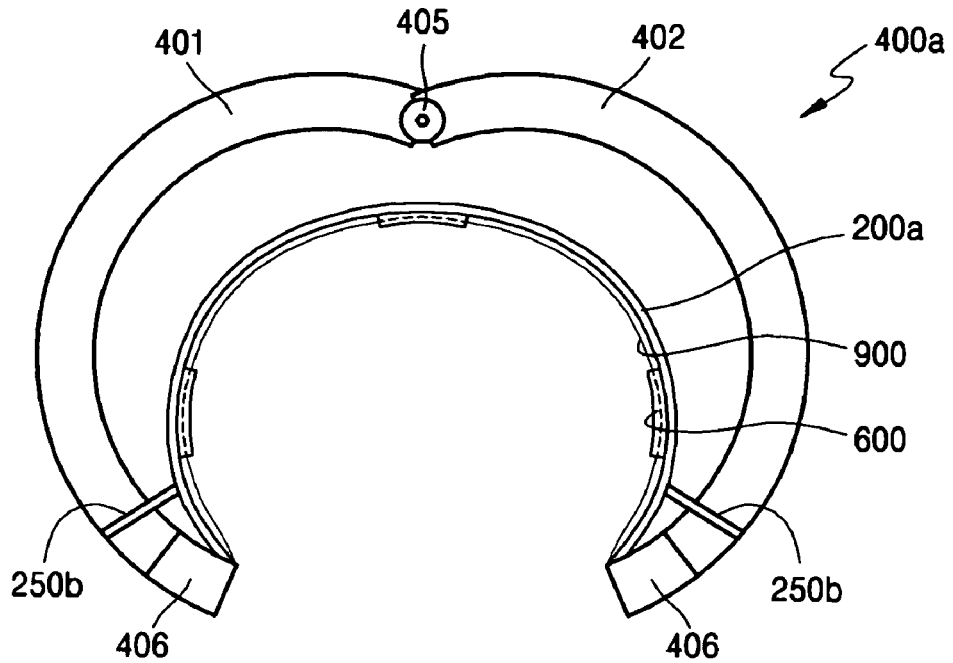
FIG. 6A is a plan view illustrating a cuff interference member according to another exemplary embodiment of the present invention before fitting the cuff.
Figure 6B:
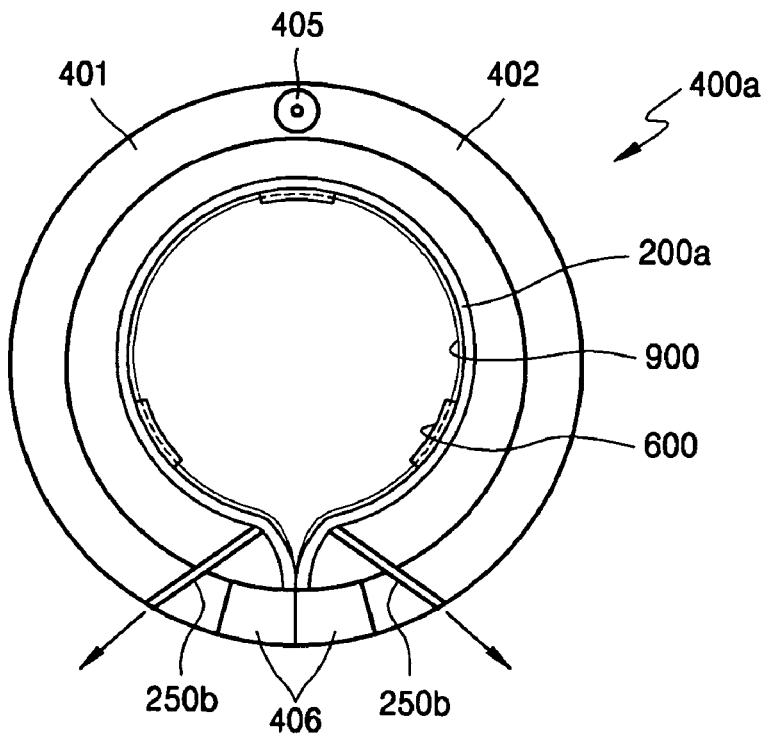
FIG. 6B is a plan view illustrating the cuff interference member after fitting the cuff.

FIGS. 5A and 6A are plan views illustrating the auxiliary decompressing means according to an exemplary embodiment of the present invention before fitting the cuff 200a, and FIGS. 5B and 6B are plan views illustrating the auxiliary decompressing means after fitting the cuff 200a. FIGS. 5A and 5B show the cuff interference member 250a rotatably coupled to the cuff fitting member 400a, and FIGS. 6A and 6B show the cuff interference member 250b slidably coupled to the cuff fitting member 400a. The reference numeral 200a denotes a cuff composed of one band and the reference numerals 200b denotes a cuff composed of a pair of bands. Like reference numerals denote like elements, and thus their description will not be repeated.

The cuff interference member 250a or 250b contacts and interferes with the cuff 200a or 200b to provide a compressing pressure at the initial time of fitting. The cuff interference member 250a or 250b is then rotated or slid over time, and performs the mechanical decompressing function in addition to the decompressing function due to the viscoelasticity of the cuff 200a or 200b.

The pressure adjusting means according to an exemplary embodiment of the present invention may further include an auxiliary decompressing means. As an example of the auxiliary decompressing means, a cuff hole and a cuff cam are provided in the cuff fitting member.

In an exemplary embodiment of the present invention, the cuff is composed of a pair of bands, with one end fixed respectively to the first and second pieces, and the other ends free. Here, the pressure adjusting means further includes a cuff hole formed in the hinge member so as to pass the free ends; and a cuff cam formed in the hinge member so as to compress the free ends when the first and second pieces are unlocked and to release the free ends when the first and second pieces are locked. The cuff hole and the cuff cam further enhance the amount of decompression of the cuff due to its viscoelasticity.

Figure 7A:
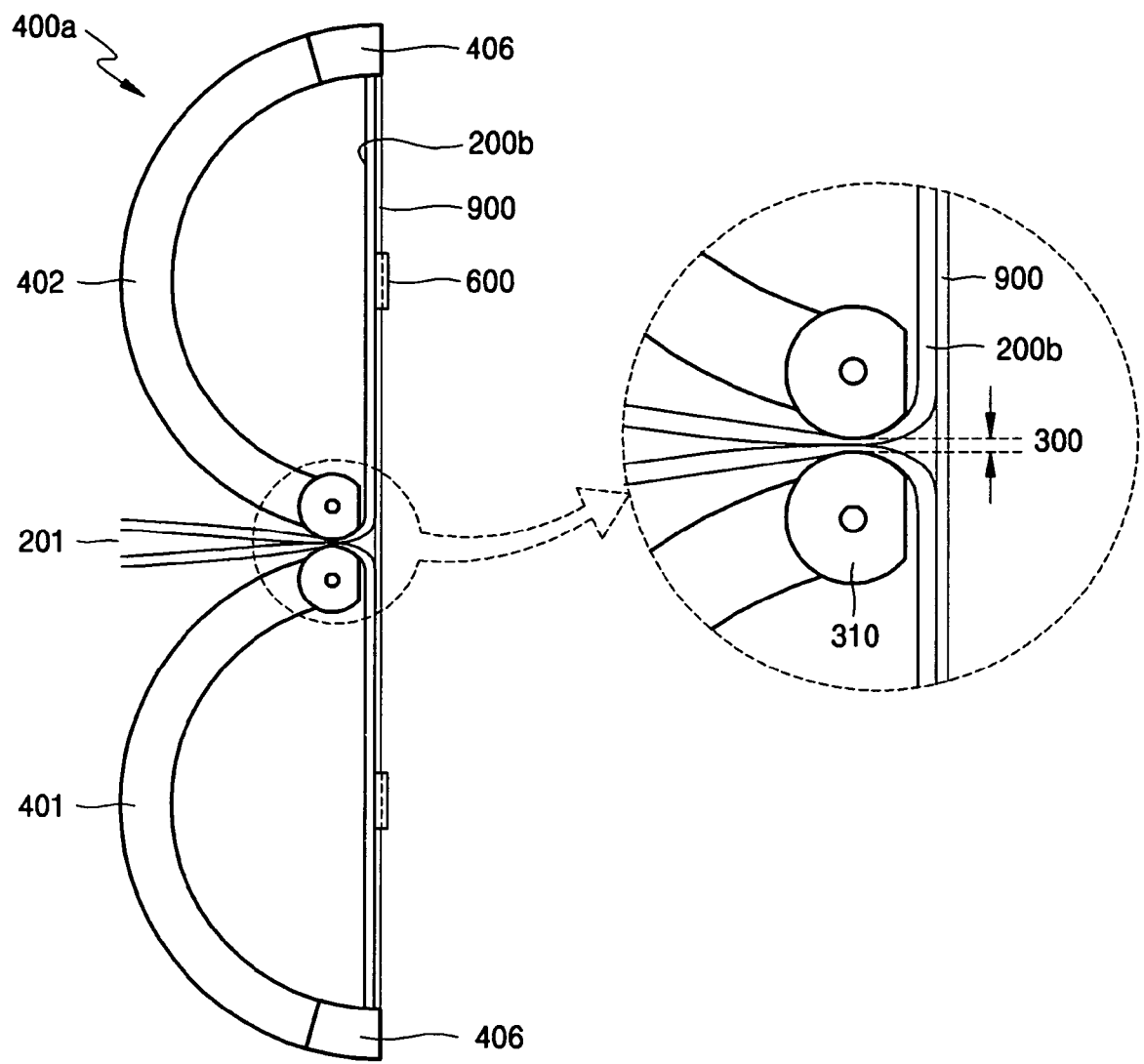
FIG. 7A is a plan view illustrating a cuff interference member according to another exemplary embodiment of the present invention before fitting the cuff.
Figure 7B:
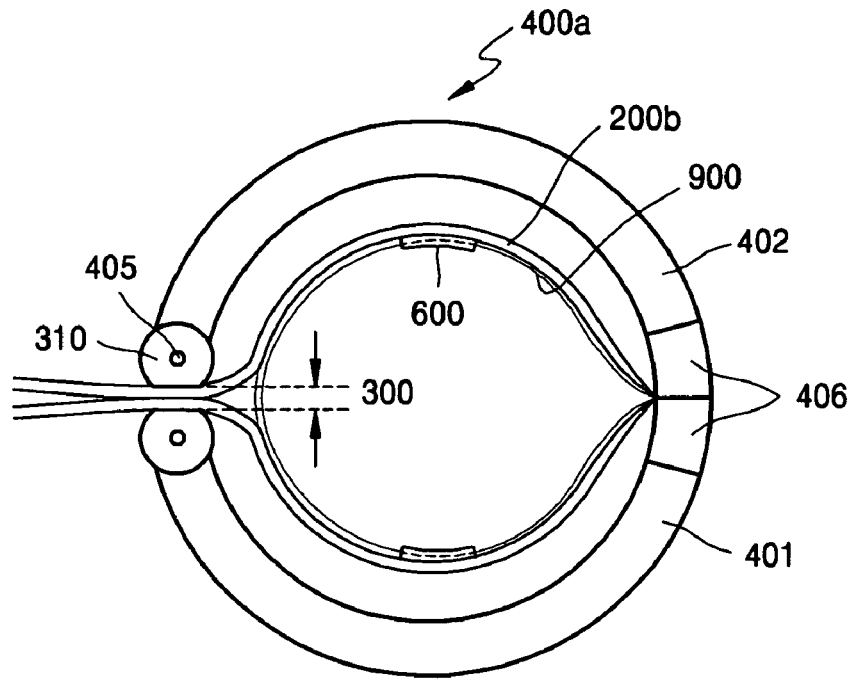
FIG. 7B is a plan view illustrating the cuff interference member after fitting the cuff.

FIG. 7A is a plan view illustrating a state before fitting the cuff 200b, and FIG. 7B is a plan view illustrating a state after fitting the cuff 200b. The cuff 200b denoted by the reference numeral 200b in FIGS. 7A and 7B is composed of a pair of bands, with one end fixed respectively to the ends of the first and second pieces 401 and 402, and the other end free. Before fitting the cuff 200b, the free end 201 is pulled and a tension is applied to the cuff 200b at the portion from the hinge member 405 to the ends of the first and second pieces 401 and 402. The cuff cam 310 has a D shape in which a part of an ellipse is cut out, and includes a convex portion and a concave portion. The free ends 201 pass through the cuff hole 300.

Before fitting the cuff 200b, the first and second pieces 401 and 402 are not locked, and the free ends 201 are pressed toward the cuff hole 300 by the convex portion of the cuff cam 310. The cuff 200b, of which the free ends 201 are compressed, is restricted and expanded as it comes in contact with the body part fitted with the cuff 200b.

When the first and second pieces 401 and 402 are rotated in the locking direction at the same time as fitting the cuff 200b, the cuff 200b surrounds and compresses the body part. When the first and second pieces 401 and 402 are locked, the concave portion of the cuff cam 310 releases the free ends 201. Accordingly, mechanical decompression is performed in addition to the decompression due to the viscoelasticity of the cuff 200b.

The pressure adjusting means according to the present invention further includes an auxiliary decompressing means. A cuff driving unit is provided as an example of the auxiliary decompressing means.

In an exemplary embodiment of the present invention, the cuff is composed of a pair of bands with one end of each free, and the pressure adjusting means further includes a cuff fitting member fixing the other end of the cuff, and a cuff driving unit that pulls the free end so as to compress the body part fitted with the cuff at the initial time of fitting the cuff and then gradually release it over time, so as to further enhance the amount of decompression of the cuff due to the viscoelasticity.

Here, the cuff driving unit may include a cuff driving axis around which the free end of the cuff is wound, and the cuff driving unit adjusts the compressing pressure and the decompressing pressure by rotating the cuff driving axis.

Figure 8:
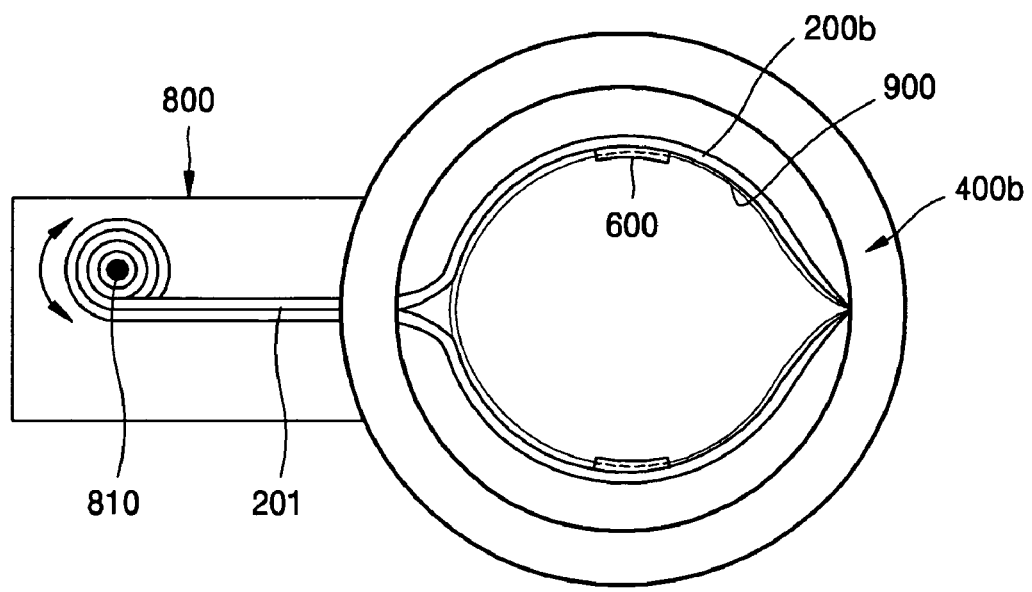
FIG. 8 is a plan view illustrating an exemplary embodiment of a cuff driving unit according to the present invention.

FIG. 8 is a plan view illustrating an exemplary embodiment of the cuff driving unit according to the present invention. The cuff fitting member 400b shown in FIG. 8 has a circular ring shape, but is not limited to this embodiment, and may be divided into the first and second pieces 401 and 402. The free end 201 of the cuff 200b is wound around the cuff driving axis 810. The cuff driving unit 800 rotates the cuff driving axis 810 under the control of the control unit 950 to adjust the amount of compression and decompression in response to the signals measured by the blood pressure sensor 600 and the blood flow sensor 900.

Figure 10:
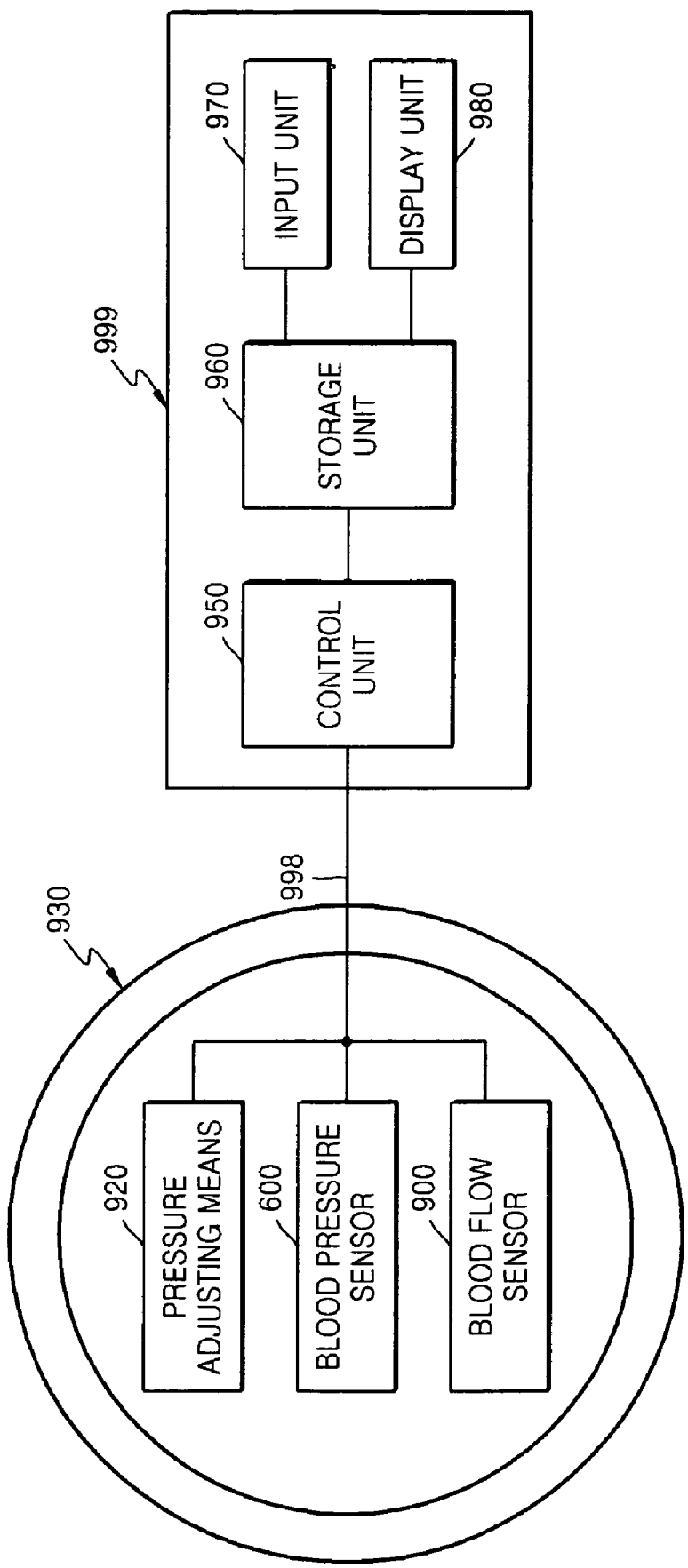
FIG. 10 is a block diagram illustrating a mobile terminal having the blood pressure meter according to an exemplary embodiment of the present invention.
Figure 11:
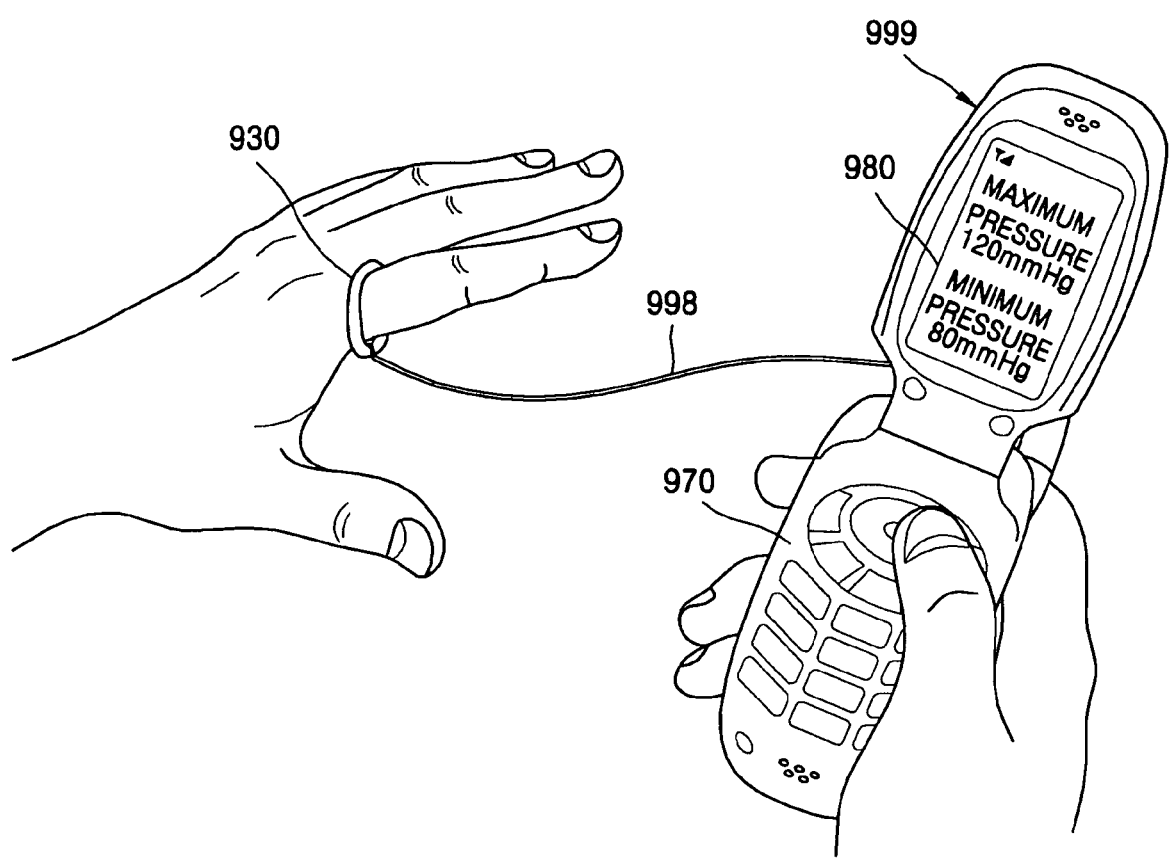
FIG. 11 is a perspective view illustrating a mobile terminal having the blood pressure meter according to an exemplary embodiment of the present invention.

FIG. 10 is a block diagram illustrating a mobile terminal having the blood pressure meter according to an exemplary embodiment of the present invention. FIG. 11 is a perspective view illustrating an example where a testee measures their blood pressure with the mobile terminal having the blood pressure meter. The mobile terminal having the blood pressure meter includes a mobile terminal body 999 and a blood pressure measuring unit 930. The mobile terminal body 999 includes a display unit 980 for displaying the measured blood pressure. The blood pressure measuring unit 930 is connected to the mobile terminal body 999. The blood pressure measuring unit 930 includes the pressure adjusting means 920, the blood pressure sensor 600, and the blood flow sensor 900. The pressure adjusting means includes the cuff 200a or 200b and the cuff fitting member 400a or 400b. The pressure adjusting means may further include the auxiliary decompressing means.

The control unit 950 may be provided in the blood pressure measuring unit 930 or the mobile terminal body 999. In FIG. 10, the control unit 950 is provided in the mobile terminal body 999. The mobile terminal body 999 may further include a storage unit 960, an input unit 970, and a display unit 980. The blood pressure measuring unit 930 may be detachably connected to the mobile terminal body 999. An element 998 connecting the blood pressure measuring unit 930 and the mobile terminal body 999 denotes a wired connection means or a wireless communication means using infrared rays. The wireless communication means is well known to those skilled in the art and thus a description thereof will be omitted.

When a testee inputs information necessary for measuring their blood pressure to the input unit 970, the input information is displayed on the display unit 980 and stored in the storage unit 960. For example, measuring time, nothing of repeated measurement, and repeated measurement periods are input. The control unit 950 controls the blood pressure meter in accordance with the information stored in the storage unit 960. The control unit 950 calculates the maximum blood pressure and the minimum blood pressure from the signals measured by the blood pressure sensor 600 and the blood flow sensor 900. The calculated blood pressure is stored in the storage unit 960 and output to the display unit 980.

Examples of the mobile terminal body 999 may include a mobile phone, a portable computer, and a wristwatch. The blood pressure measuring unit 930 can be attached to and detached from the mobile terminal body 999 at any time. The testee can easily measure their blood pressure at any time to manage their health.

An example of the application of the mobile terminal having the blood pressure meter according to an exemplary embodiment of the present invention will now be described. At a certain time every day, the control unit 950 informs the testee that it is time to measure their blood pressure. The testee fits the cuff 200*a* or 200*b* to their finger and connects the blood pressure measuring unit 930 to the mobile terminal body 999. The control unit 950 controls the blood pressure sensor 600 and the blood flow sensor 900 to calculate the blood pressure in accordance with the measured signals. The calculated blood pressure is stored in the storage unit 960. The blood pressure stored in the storage unit 960 can be cumulatively managed, thereby checking the testee's health condition. When the mobile terminal body 999 has a communication function, the measured blood pressure can be transmitted to a doctor or a health management server, the health condition can be checked, and the result can be returned to the testee.

As described above, in the blood pressure meter and the mobile terminal having the blood pressure meter according to an exemplary embodiment of the present invention, since the blood pressure is measured with the cuff made of a viscoelastic material instead of the conventional air-pressure cuff, it is possible to decrease the size of the blood pressure meter, to improve the portability. In addition, since the cuff can be decreased in size while maintaining the signal-to-noise ratio, it is possible to accurately measure the blood pressure with the cuff fitted to a finger. The reliability in measuring the blood pressure can be improved by providing the blood flow sensor, and desired compression and decompression conditions corresponding to the health condition of the testee can be prepared by utilizing the viscoelasticity of the cuff and the auxiliary decompressing means. Since the mobile terminal body and the blood pressure measuring unit can be detachably connected, the blood pressure can be measured at any time.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. A blood pressure meter comprising:

a pressure adjusting member comprising a cuff that is elastically deformed at a time of fitting the cuff onto a body part of a testee to compress the body part and impede blood flow, and whose compressing pressure to the body part is decreased over time due to its viscoelasticity;

a blood pressure sensor that measures the pressure of the body part at a time of compression and decompression of the pressure adjusting member; and a control unit that analyzes a signal measured by the blood pressure sensor at the time of compression and decompression of the pressure adjusting member and calculates the blood pressure of the testee, wherein the pressure adjusting member further includes a cuff fitting member having first and second pieces with lockers provided at one end of each piece, and of which the other ends are coupled to each other with a hinge member, wherein the first and second pieces are locked to each other though the lockers at the time of fitting the cuff, and the first and second pieces are unlocked and opened about the hinge member at the time of removing the cuff, wherein the pressure adjusting member further includes a cuff interference member that is rotatably provided in the cuff fining member, that contacts and interferes with the cuff in a direction in which it is adapted to come in close contact with the body part at the initial time of fining the cuff, and that is rotated in the inversed direction over time, and wherein the cuff interference member further enhances the amount of decompression of the cuff.

2. A blood pressure meter comprising:

a pressure adjusting member comprising a cuff that is elastically deformed at a time of fining the cuff onto a body part of a testee to compress the body part and impede blood flow, and whose compressing pressure to the body part is decreased over time due to its viscoelasticity;

a blood pressure sensor that measures the pressure of the body part at a time of compression and decompression of the pressure adjusting member; and a control unit that analyzes a signal measured by the blood pressure sensor at the time of compression and decompression of the pressure adjusting member and calculates the blood pressure of the testee, wherein the pressure adjusting member further includes a cuff fining member having first and second pieces with lockers provided at one end of each piece, and of which the other ends are coupled to each other with a hinge member, wherein the first and second pieces are locked to each other through the lockers at the time of fining the cuff, and the first and second pieces are unlocked and opened about the hinge member at the time of removing the cuff, wherein the pressure adjusting member further includes a cuff interference member that is slidably provided in the cuff fitting member, that contacts and interferes with the cuff in a direction in which it is adapted to come in close contact with the body part at the initial time of fitting the cuff, and that is slid in the inversed direction over time, and wherein the cuff interference member further enhances the amount of decompression of the cuff.

3. A blood pressure meter comprising:

a pressure adjusting member comprising a cuff that is elastically deformed at a time of fitting the cuff onto a body part of a testee to compress the body part and impede blood flow, and whose compressing pressure to the body part is decreased over time due to its viscoelasticity;

a blood pressure sensor that measures the pressure of the body part at a time of compression and decompression of the pressure adjusting member; and a control unit that analyzes a signal measured by the blood pressure sensor at the time of compression and decompression of the pressure adjusting member and calculates the blood pressure of the testee, wherein the pressure adjusting member further includes a cuff fitting member having first and second pieces with lockers provided at one end of each piece, and of which the other ends are coupled to each other with a hinge member, wherein the first and second pieces are locked to each other through the lockers at the time of fitting the cuff, and the first and second pieces are unlocked and opened about the hinge member at the time of removing the cuff, wherein the cuff is composed of a pair of bands, with one end of each of respective bands of the pair of bands fixed respectively to one end of the first and second pieces, and the other end of each of the respective bands free, wherein the pressure adjusting member further includes:

a cuff hole formed in the hinge member so as to pass the free ends; and a cuff cam formed in the hinge member so as to compress the free ends when the first and second pieces are unlocked and release the free ends when the first and second pieces are locked, and wherein the cuff hole and the cuff cam further enhance the amount of decompression of the cuff.

4. The blood pressure meter according to claim 1, wherein the pressure adjusting member further includes an auxiliary decompressing means for further enhancing the amount of decompression of the cuff.

5. A blood pressure meter comprising:

a pressure adjusting member comprising a cuff that is elastically deformed at a time of fitting the cuff onto a body part of a testee to compress the body part and impede blood flow, and whose compressing pressure to the body part is decreased over time due to its viscoelasticity;

a blood pressure sensor that measures the pressure of the body part at a time of compression and decompression of the pressure adjusting member; and a control unit that analyzes a signal measured by the blood pressure sensor at the time of compression and decompression of the pressure adjusting member and calculates the blood pressure of the testee, wherein the cuff is composed of a pair of bands, and one end of the cuff is free, and wherein the pressure adjusting member further includes a cuff fitting member that fixes the other end of the cuff; and a cuff driving unit that pulls the free end so as to compress the body part fitted with the cuff at the initial time of fitting the cuff, and releases the free end over so as to further enhance the amount of decompression of the cuff due to the viscoelasticity, wherein the cuff driving unit includes a cuff driving axis around which the free end of the cuff is wound, and wherein the cuff driving unit adjusts the compressing pressure and the decompressing pressure by rotating the cuff driving axis.

* * * * *